United States Patent [19]

Luukkala et al.

[11] Patent Number: 4,882,499
[45] Date of Patent: Nov. 21, 1989

[54] FIBER-OPTIC DETECTOR FOR OILS AND SOLVENTS

[75] Inventors: Mauri Luukkala, Espoo; Aarre Matilainen, Helsinki; Jarmo Viirto, Nummela, all of Finland

[73] Assignee: Soundek Oy, Finland

[21] Appl. No.: 166,386

[22] Filed: Mar. 10, 1988

[30] Foreign Application Priority Data

Mar. 10, 1987 [FI] Finland .................................. 871042

[51] Int. Cl.$^4$ ........................................... G01N 15/06
[52] U.S. Cl. .................................... 250/577; 250/227; 73/293
[58] Field of Search ................ 250/227, 577; 340/619; 73/293

[56] References Cited

U.S. PATENT DOCUMENTS 4,159,420  6/1979  Tsunoda .
4,386,269  5/1983  Murphy .

FOREIGN PATENT DOCUMENTS 0126600  11/1984  European Pat. Off. .
WO86/05589  9/1986  PCT Int'l Appl. .
2103786  2/1983  United Kingdom .

*Primary Examiner*—Edward P. Westin
*Assistant Examiner*—Khaled Shami
*Attorney, Agent, or Firm*—Steinberg & Raskin

[57] ABSTRACT

A liquid detector utilizing fiber optics, by which the presence of oils and various solvents can be detected. The detector is internally safe because the optical fiber is an insulator and may therefore be used to monitor liquids involving fire or explosive hazards. The detector may be used to detect leakage when storing oils and solvents, because it reacts most rapidly with these liquids. The detector makes use of capillarity of a sensing pick-up thereof, the optical reflection coefficient of the pick-up material changing as the pick-up material comes into contact with the liquid to be detected.

6 Claims, 1 Drawing Sheet

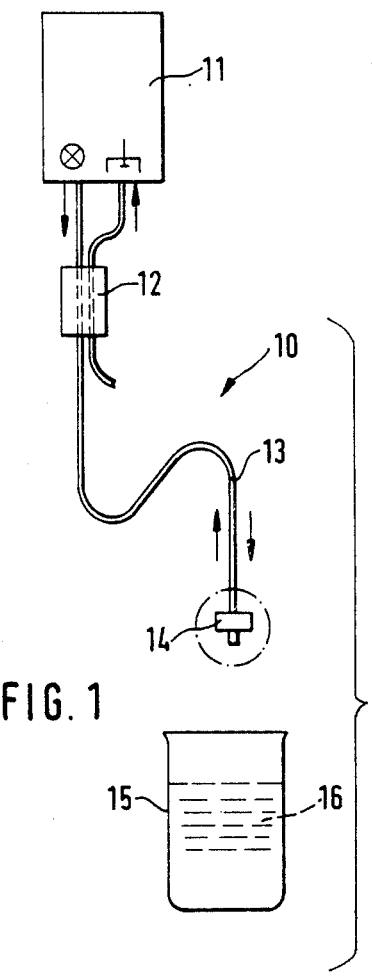
FIG. 1
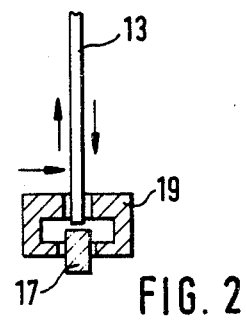
FIG. 2
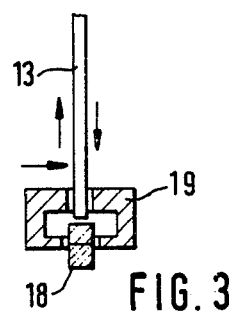
FIG. 3
FIG. 4
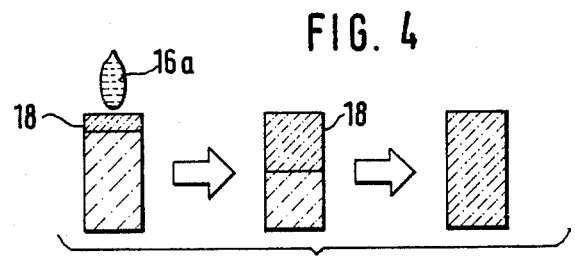

FIBER-OPTIC DETECTOR FOR OILS AND SOLVENTS

BACKGROUND OF THE INVENTION

The present invention is directed to a fiber-optic detector for oils, solvents, and equivalent liquid hydrocarbons, comprising a fiber-optic light transmitter and light receiver, and an optical fiber connected to the same, along with a pick-up for sensing the liquids located at the free end of the optical fiber.

It is possible with this type of apparatus utilizing fiber-optics to detect various kinds of liquids swiftly and safely, especially various oils such as light or heavy fuel oil, or equally other liquids presenting fire or explosive hazards such as solvents. This means are particularly well usable in providing alarm of liquid leakage, because such means have a fairly high speed of detection.

In the chemical industry, dangerous and inflammable liquids, above all, often have to be stored in big cisterns both outdoors and indoors. Because of leakage, such a cistern constitutes a considerable risk to safety of humans as well as nature in general. Electronic detection, particularly of liquids posing risk of fire or explosion, is difficult because an electronic, galvanic measuring and alarm pick-up, involves risk of short-circuiting and sparking. The leakage detector should be "internally safe". This is achievable by using fiber-optics. The fiber is an insulator, and is otherwise completely passive, so that it cannot suffer short-circuiting or cause sparking.

Detection of oils and oil leakage is also rather difficult for the reason that oil is rather passive and, for example, its dielectric constant is little different from that, e.g., of sandy oil. Oil leakage is not observed in general until it is too late. Detection of small leaks may be particularly difficult because it may be hard to notice the leak by the liquid level, e.g. in a large cistern. Moreover, if quick-evaporating liquids are concerned, which are constituted by many kinds of solvents, then the substance may evaporate before the leakage is noticed. The means for detecting leakage should therefore be quite sensitive and fast. Such means provided by the present invention will, for instance, detect acetone within about one second, and fuel oil in less than half a minute. These speeds are adequate.

U.S. Pat. No. 4,386,269 discloses a detector in which a special sheath layer is provided for the fiber, in which the refractive index differs from the refractive index of the fiber itself so that the light is reflected or refracted into the fiber. When such a sheath layer is made oil-absorbing, its refractive index changes so that light will "leak out" and light propagation properties within the fiber change so that it is totally absorbed. It is essential that the oil-absorbing layer is in contact with the core of the fiber in order that the condition for total reflection might be altered. The relationship between the refractive index of the fiber and of its sheath change in a given manner, so that the condition of total reflection is no longer fulfilled for the core and the sheath in immediate contact therewith.

In a detector disclosed in U.S. Pat. No. 4,159,420, a fiber is used which has a refractive index higher than that of the surrounding matter. The fiber is surrounded with a material of which the refractive index changes when it comes into contact, e.g., with oil. This change of refractive index has the effect that the condition of total reflection in the core of the fiber is no longer fulfilled and the light "leaks out", thus causing considerable extra attenuation in the propagation of light. On the end of the fiber, a mirror may be installed, the reflection from the mirror returning the light to its starting point, whereby the change of refractive index can be observed when the light is reflected by the walls of the fiber. It is essential that the relationship of the refractive indices of the fiber core and of its sheath change in a given manner, so that the condition of total reflection is no longer fulfilled for the core and for the sheath in immediate contact therewith.

In E.P. Application No. 126,600, optical fibers are employed to observe the presence of certain chemicals by using on an end of the pick-up, a pick-up construction of such kind wherein the end of the fiber bundle is tightly surrounded by a porous membrane inside which powdery, cross-linked polystyrene has been provided. To such polystyrene powder, a reagent has been chemically bound which changes color on contact with the liquid to be monitored. The porous membrane consists of Teflon, which repels water. The chemical to be monitored passes through the Teflon film and reacts with the substance provided in the polystyrene powder, the spectroscopic characteristics of the substance changing on contact with the liquid.

In reference WO 86/05589, a material is used to which an indicator substance has been permanently attached of which the spectral characteristics change when it comes into contact with the substance to be monitored.

G.B. Pat. No. 21 03 786 discloses a detector in which the surface of the fiber core has been covered with an indicator substance having a porous surface. The end of the optical fiber is provided with a mirror which reflects the light back to the measuring electronics.

It may be noted regarding the prevailing state of the art, that it is previously known that optical fibers may be used to observe sensor elements installed on the end of the fiber. Light is sent from an optical fiber transmitter by the fiber to the object to be examined, and the light is returned back to a detector along the same, or another fiber. The sensor element on the end of the fiber is then affected in one way or another by the phenomenon that is being examined.

A leakage detector is known in the art which detects the presence of oils based on the circumstance that the sheath material of the optical fiber consists of a material which swells as it comes onto contact with oil. The oil then gains access to the space between the sheath and fiber, thus causing extra attenuation in the propogation of light.

SUMMARY OF THE INVENTION

Accordingly, it is an object of the present invention to achieve improvement over previously-known fiber-optic detectors.

It is a more detailed object of the present invention to provide a detector which is "internally safe".

It is still a further object of the present invention to provide a detector which is extremely sensitive and quick in detecting a liquid, e.g. a liquid spill.

These and other objects are attained by the present invention, which is directed to a fiber optic detector for liquids, comprising a fiber-optic light transmitter/receiver, and optical fiber attached to the transmitter/receiver, and a pick-up located on a free end of the fiber for sensing liquid. At least a portion of the pick-up is formed of material which, when coming into contact with the liquid to be detected, either absorbs the liquid by capillarity, or becomes dissolved in the liquid. Thus, an optical reflection coefficient of the pick-up material changes, which is observed by the detector.

Accordingly, the objects of the present invention are attained with a detector which is principally characterized by the sensor pick-up being formed either of such material which, on coming into contact with the liquid to be monitored, absorbs the liquid by capillary action, or of a material which dissolves in the liquid to be monitored, whereby the optical coefficient of reflection of the pick-up material changes so that it can be observed by means of a fiber-optic detector in a manner known in and of itself in electro-optics.

Other important characteristics and features of the detector of the present invention are further described below.

BRIEF DESCRIPTION OF THE DRAWINGS

The present invention will be described in further detail below referring to certain advantageous embodiments thereof, illustrated in the figures, to which however the present invention is not intended to be exclusively confined. In the figures, FIG. 1 is a schematic illustration of an advantageous embodiment of a fiber-optic detector of the present invention;

FIG. 2 is a view, on a larger scale, of an advantageous embodiment of a sensing pick-up employed in the fiber-optic detector of FIG. 1;

FIG. 3 is a view on a larger scale of another advantageous embodiment of the sensing pick-up employed in the fiber-optic detector in FIG. 1; and FIG. 4 schematically illustrates the absorption of a liquid droplet and travel thereof from a stained end of a sensor pick-up, with the aid of capillary force to the other end of the porous pick-up material, the stain following therealong.

DESCRIPTION OF THE PREFERRED EMBODIMENTS

An inventive feature of the present detector is a drastic change of the optical coefficient of reflection of the pick-up mounted on an end of an optical fiber, when the pick-up comes into contact with oil or a solvent, so that the change of optical contrast can be observed by fiber-optic means. The change of optical reflection coefficient can naturally be observed, e.g., with a combination of LED lamp and photo diode, however any such arrangement is not internally safe in view of explosive liquids. A device of such type could also hardly be buried in the ground, in contrast to a passive fiber pick-up.

Fiber-optics transmitters and receivers are known from fiber-optics, by which objects can be observed through fibers. They constitute an important part of the present invention. Such arangements are previously known in and of themselves. Furthermore, fiber-optic directional switches are utilized, by which the light arriving from the pick-up can be separated from the transmission light travelling along the same fiber.

There is a plurality of fibrous substances which take up liquids by absorption with the aid of capillary force, and change color. As an example, a lump of sugar dipped in a coffee cup, can be considered. The sugar lump rapidly absorbs coffee and turns dark The dark discoloration is observable by fiber-optics. Furthermore, if the sugar lump is held long in the coffee, it will totally dissolve away, and this too can be observed by fiber optics.

This feature is likewise a part of the present invention. However, when the intent is to observe oils or other liquid hydrocarbons, e.g. among sand, then the pick-up must be water-repellent but at the same time hydrocarbon-absorbing. In this case, the pick-up material should be hydrophobic, preferably white in color, and the pores in the substance should be of suitable size. It is possible to sinter porous bodies from polystyrene, which have the exactly required properties. If a porous polyethylene capsule is submerged in water-soluble ink, it will remain white, whereas it turns immediately dark on immersion in alcohol-soluble ink. Sintered polyethylene is otherwise mechanically durable.

There are still other porous materials, e.g. the material of felt pen tips, and porous Teflon (polytetrafluoroethylene) film (Bore Tex), which possess the desired properties. The desired hydrophobic quality and capillarity depend basically upon the surface tension properties of the material at the interface between two substances.

Tests have been carried out with sintered polyethylene capsules, e.g. in such a manner that the pick-up has been buried in sandy soil one year, without any changes in operation. Optical fibers do tolerate burying in the ground provided that certain protective steps are taken. It is clear that the pick-up head proper has to be mechanically protected to that it is not subjected to any stress. A thin oil layer floating on the water can also be detected with the aid of the pick-up.

Another alternative for observing liquids is to use a material which is rapidly dissolved therein. In its simplest form, a pick-up of this type is a white click of paint applied on an end of the fiber, which will rapidly dissolve, e.g. in acetone, when it comes into contact therewith. By the effect of the dissolving, the reflection is drastically reduced and an alarm is obtained.

The pick-ups just described are naturally good for only single or one-time use. In practical implementations, these are constructed to be exchangeable with ease. This is not a drawback, in that leakage is usually also a singular occurrence or event.

It may also be noted that the measured "on/off" ratios have been better than 20 dB, which makes for an adequate margin regarding any extra attenuations that may occur in the fibers, for instance due to flexure. However, the fiber is most often protected, e.g. with a protective tube against external effects.

Referring to FIG. 1, a fiber-optic transmitter/receiver 11 sends light into a fiber 13 at a suitable wavelength, towards a pick-up 14 on a free end of the fiber 13, so that the light returning from the pick-up end enters the receiver 11 through an optical directional switch 12. It may be noted in this connection that the detector 10 of the present invention operates equally well with two separate fibers, one of them being a transmitting fiber and the other being a receiving fiber, however this does not substantially alter the present invention herein. A liquid 16 in a vessel 15 represents the liquid which must be detected. The liquid 16 may naturally be, for instance, liquid that has been spilled onto the ground, and comes into contact with the pick-up 14.

FIGS. 2 and 3 illustrate in closer detail the design of the pick-up head 17 proper. On the end of the fiber 13, the pick-up proper 17 has been mounted with the aid of a holder or sleeve 19. The fiber 13 is used to monitor the optical reflecting layer on the top surface of the pick-up material. The pick-up material is a porous material so that, when it comes into contact with the liquid 16, the liquid 16 is drawn or absorbed by the aid of capillary phenomenon into the pick-up material, whereby the optical reflection coefficient of the pick-up material top surface changes. It is thus understood that the capillary force occurring in the porous material moves part of the liquid 16 to a location close to the end of the fiber 13. Since the end of the fiber 13 can be isolated from the liquid 16 itself, it is not necessarily soiled.

If the liquid 16 to be monitored causes only a minor change in the coefficient of reflection, the change of contrast can be boosted by staining the pick-up material with a suitable staining agent 18, in which the staining agent 18 will travel to the end of the fiber 13 along with the liquid 16, as can be seen in FIG. 3. This may be a good procedure in detecting colorless solvents, such as acetone, ethanol or equivalent.

In FIG. 4, the absorption of a liquid droplet 16a and its travel from the stained end of the pick-up 17 by capillary effect to the other end of the porous pick-up material, is more closely illustrated, with the staining agent 18 following along. The staining agent 18 must be soluble in the respective liquid 16. The staining agent may be ink or equivalent.

When the fiber-optic transmitter/receiver unit 11 observes a change in the optical reflection coefficient, an alarm signal indicating the event or occurrence is obtained from electronics in a manner known in and of itself. It is clear from what has been described above that the pick-up material is decisive for operation.

The preceding description of the present invention is merely exemplary, and is not intended to limit the scope thereof in any way.

What is claimed is:

1. A fiber optic detector for liquids, comprising
a fiber optic light transmitter/receiver for transmitting light and receiving light.
an optical fiber attached to said transmitter/receiver, and
a pick-up located on a free end of said fiber for sensing liquid, wherein
at least a portion of said pick-up is formed of material which, when coming into contact with liquid to be detected, absorbs the liquid by capillarity, and
said sensing pick-up is stained, at one end thereof, with a staining agent which, in dry condition, is positioned away from said fiber free end, and is arranged to migrate to said fiber free end with the contacted liquid,
whereby, when said pick-up contacts the liquid to be detected, said staining agent travels along with the liquid being absorbed, to an unstained end of said sensing pick-up at said free end of said fiber, and
an optical reflection coefficient of the pick-up material changes which is thereby observed by said detector.

2. The combination of claim 1, wherein said material is porous and repels certain liquids not meant to be detected, and absorbs other liquids meant to be detected.

3. The combination of claim 2, wherein said material is sintered porous polyethylene which repels water.

4. The combination of claim 2, wherein said material is porous Teflon (polytetrafluoroethylene) film.

5. The combination of claim 1, wherein just a single optical fiber is attached to said transmitter/receiver for both transmitting light from said transmitter/receiver to said pick-up and conveying light form said pick-up back to said transmitter/receiver.

6. The combination of claim 1, additionally comprising
a pair of optical fibers coupled to said transmitter/receiver and to said pick-up,
one of said fibers being a transmitting fiber for transmitting light from said transmitter/receiver to said pick-up, and
the other of said fibers being a receiving fiber for transmitting light from said pick-up back to said transmitter/receiver.

* * * * *